(12) United States Patent
Stirpe et al.

(10) Patent No.: US 7,479,552 B2
(45) Date of Patent: Jan. 20, 2009

(54) TYPE-1 RIBOSOME-INACTIVATING PROTEIN

(75) Inventors: Fiorenzo Stirpe, Bologna (IT); Andrea Bolognesi, Bologna (IT)

(73) Assignee: Tanox Pharma B.V., Amsterdam (NL)

( * ) Notice: Subject to any disclaimer, the term of this patent is extended or adjusted under 35 U.S.C. 154(b) by 13 days.

(21) Appl. No.: 10/758,902

(22) Filed: Jan. 16, 2004

(65) Prior Publication Data
US 2004/0266994 A1 Dec. 30, 2004

Related U.S. Application Data

(63) Continuation of application No. 09/445,160, filed on Mar. 10, 2000, now Pat. No. 6,680,296.

(51) Int. Cl.
*C07H 21/04* (2006.01)
*C12Q 1/34* (2006.01)
*C12N 15/63* (2006.01)
*C12N 1/20* (2006.01)

(52) U.S. Cl. ............... 536/23.2; 435/18; 435/320.1; 435/252.3

(58) Field of Classification Search ............. None
See application file for complete search history.

(56) References Cited

FOREIGN PATENT DOCUMENTS

| | | | |
|---|---|---|---|
| AF | 93/09130 A1 | 5/1993 | |
| AF | 94/26910 A1 | 11/1994 | |
| WO | WO-95/11977 A2 | 5/1995 | |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
den Hartog et al, Cloning and expression of cDNA coding for bouganin. Eur J Biochem. Mar. 2002;269(6):1772-9.*
Barblerl, et al, "Ribosome-Inactivating proteins from plants," *Biochim., Biophys., Acta,* vol. 1154:237-282 (1993).
Nicolas, Emmanuelle et al, "An additional mechanism of ribosome-Inactivating protein cytotoxicity: degradation of extrachromosomal DNA," *Biochem., J.* vol. 327:413-417 (1997).

* cited by examiner

*Primary Examiner*—Sheridan Swope

(57) ABSTRACT

The invention relates to a novel ribosome-binding protein derived from *Bougainvillea spectabilis* having a molecular weight of about 26,000 daltons by polyacrylamide gel electrophoresis under reducing and non-reducing conditions, a pI of about 9.0, and a specified amino-terminal amino acid sequence. The invention further relates to a conjugate of the protein with a targeting ligand, such as an antibody, to form an immunotoxin. The protein and the conjugate are useful in therapy, for example, in the control of tumour cells or viruses.

8 Claims, 7 Drawing Sheets

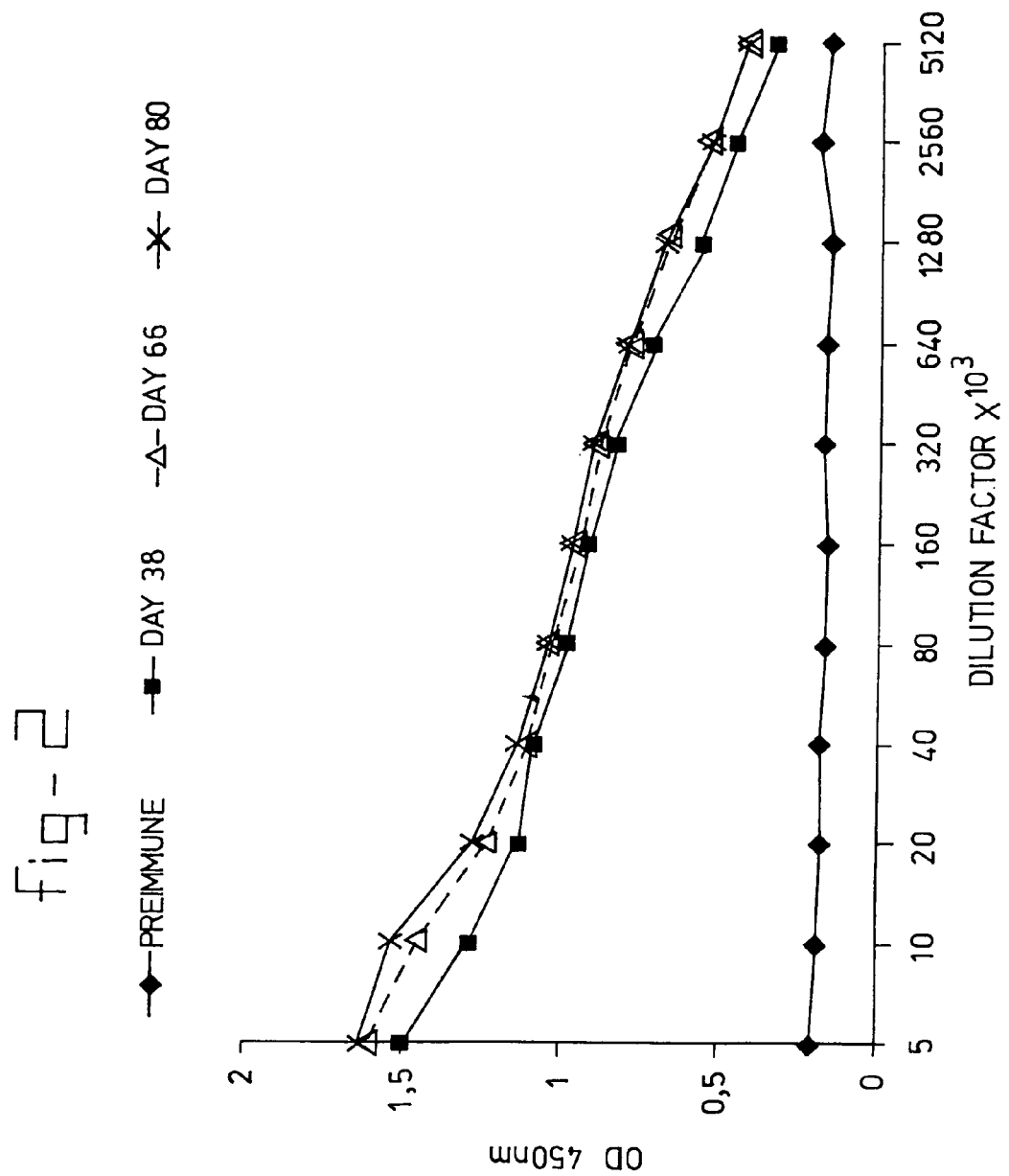

fig-3

```
bouganin                              YNTVSFNLGEAYPTFIQDLRNELAKGTP
gelonin          GLDTVSFSTKGATYITYVNFLNELRVKLKPEGN
momorcharin      DVSFRLSGADPRSYGMFIKDLRNALPFREKK
trichosanthin    DVSFRLSGATSSYGVFISNLRKALPNERKK
MAP         APTLETIASLDLNNPTTYLSFITNIRTKVADKTE
saporin     VTSITLDLVNPTAGQYSSFVDKIRNNVKDPNL
bryodin2         VDINFSLIGATGATYKTFIRNLRTTLTVGTP
bryodin1         DVSFRLSGATTTSYGVFIKNLREALPYERKK
ricin A     IFPKQYPIINFTTAGATVQSYTNFIRAVRGRLTTGAD
luffin A         DVRFSLSGSSTSYSKFIIGDLRKALPSNGT
mormordin        DVNFDLSTATAKTYTKFIEDFRATLPFSHK
PAPS        INTITFDAGNATTINKYATFMESLRNEAKDPSL
dodecandrin VNTIIYNVGSTTHISNYATFMDNLRNEAKDPSL
B.rubra RIP 2 ALDYWDLRSTTHEKYTEFIGGIRNNLKAST
B.rubra RIP 3 DDLYWDLRSTTHDKYTSFIGXIRNKLKAXT
BRIP        AAKMAKNVDKPLFTATFNVQASSADYATFIAGIRNKLRNPAH
```

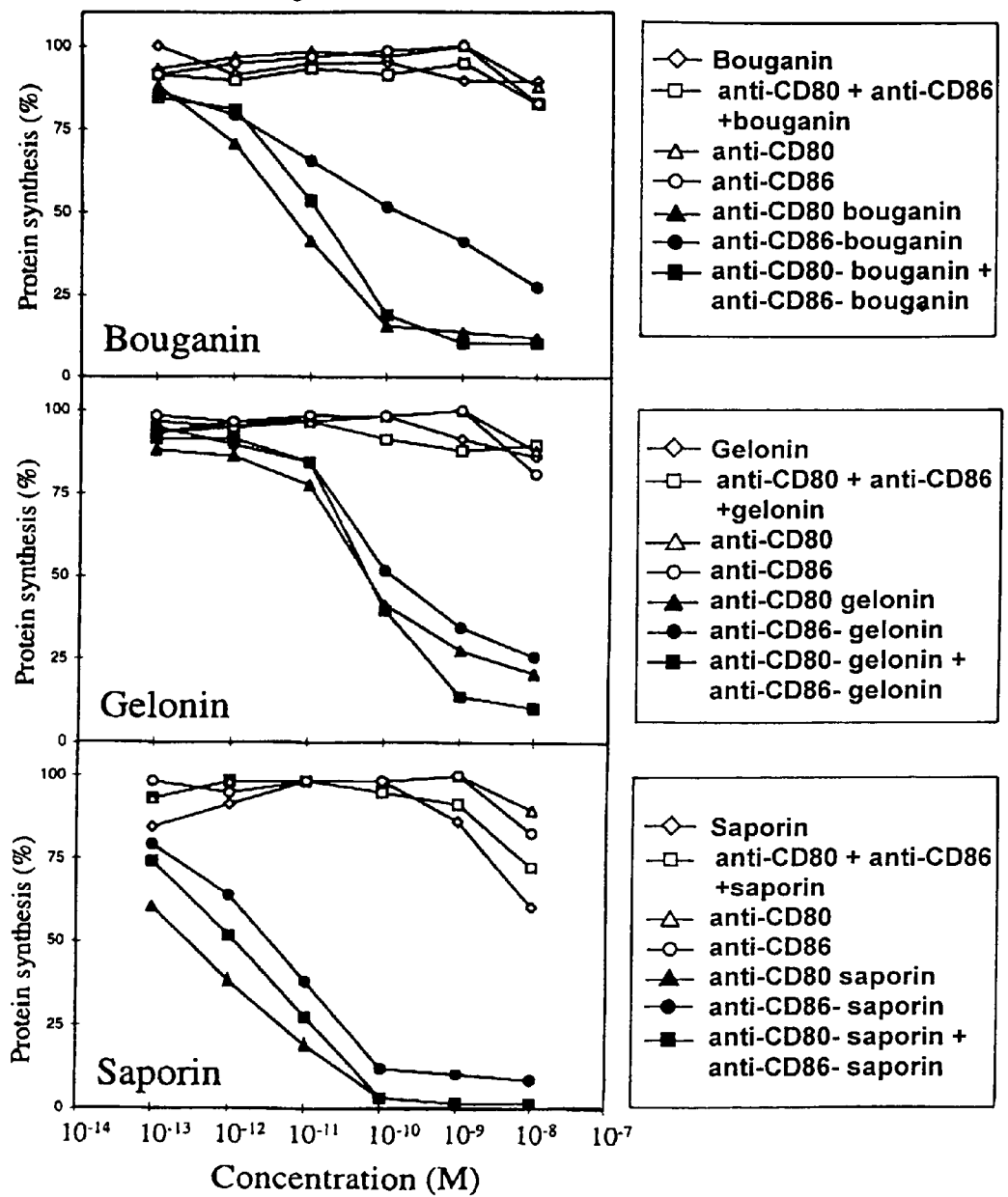

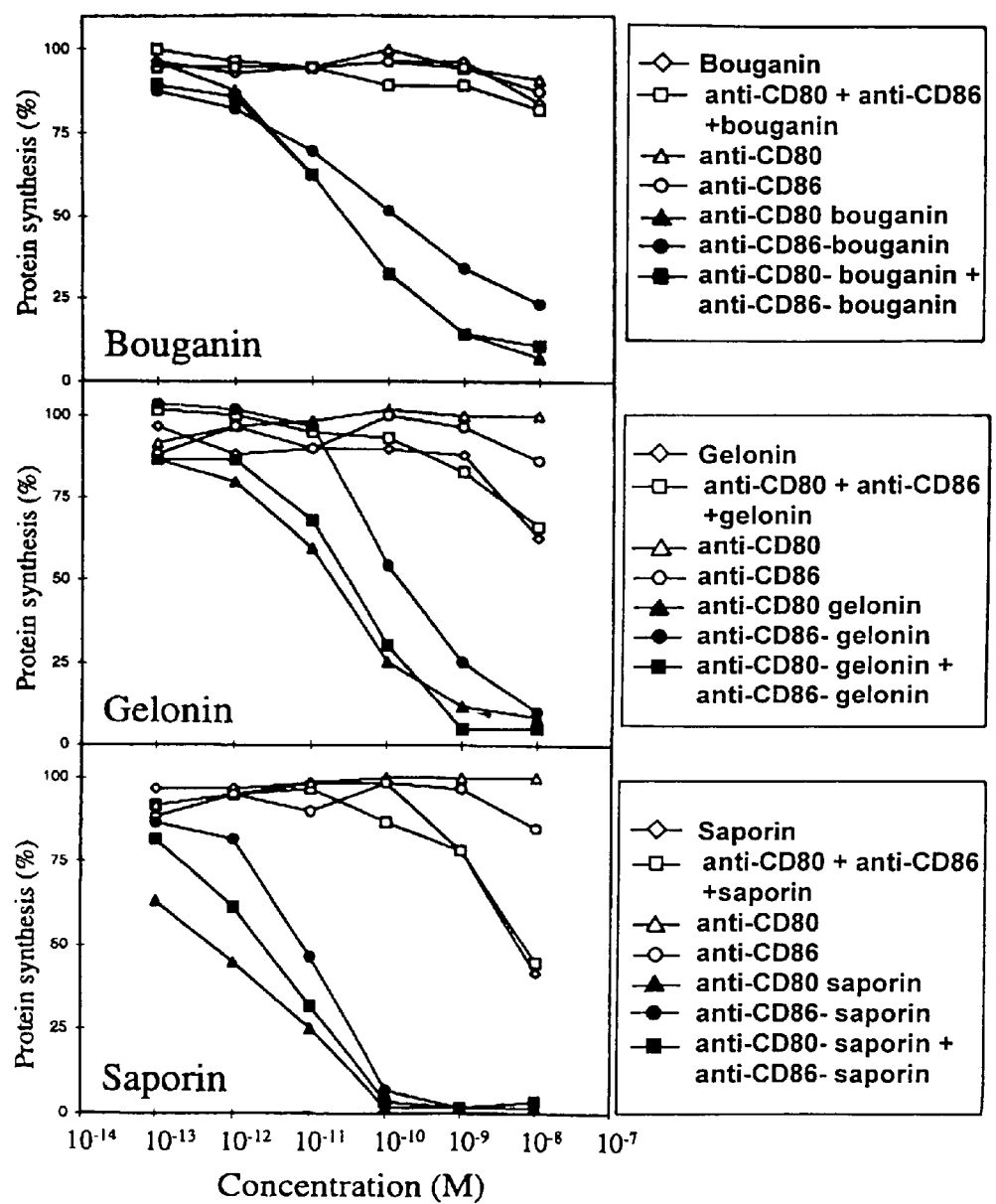

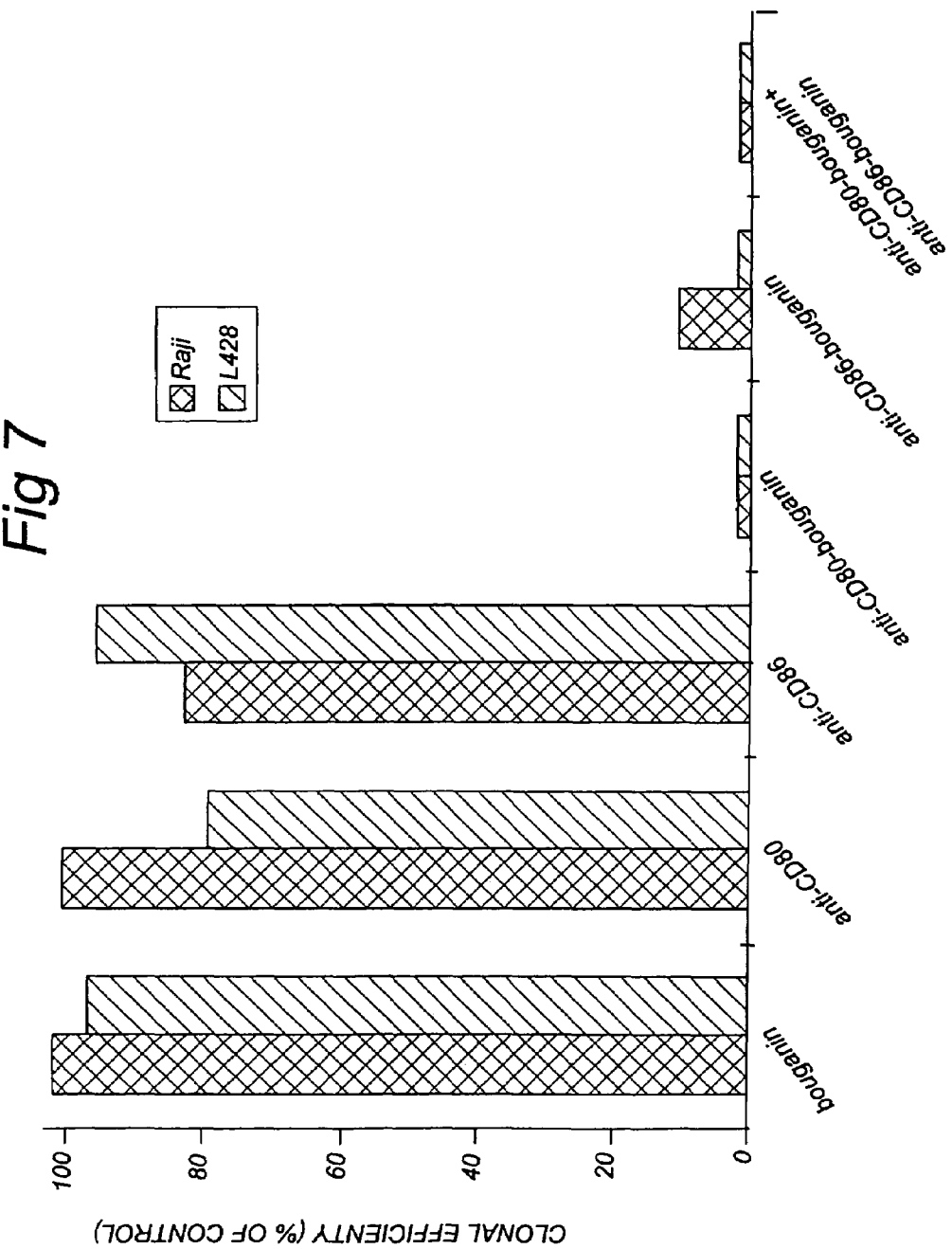

SEQUENCE LISTING

<160> NUMBER OF SEQ ID NOS: 9

<210> SEQ ID NO 1
<211> LENGTH: 30
<212> TYPE: PRT
<213> ORGANISM: Bougainvillaea Spectabilis

<400> SEQUENCE: 1

Tyr Asn Thr Val Ser Phe Asn Leu Gly Glu Ala Tyr Glu Tyr Pro Thr
 1               5                  10                  15

Phe Ile Gln Asp Leu Arg Asn Glu Leu Ala Lys Gly Thr Pro
            20                  25                  30

<210> SEQ ID NO 2
<211> LENGTH: 21
<212> TYPE: PRT
<213> ORGANISM: Bougainvillaea Spectabilis

<400> SEQUENCE: 2

Glu Leu Gly Val Tyr Lys Leu Glu Phe Ser Ile Glu Ala Ile Trp Gly
 1               5                  10                  15

Lys Thr Gln Asn Gly
            20

<210> SEQ ID NO 3
<211> LENGTH: 23
<212> TYPE: DNA
<213> ORGANISM: Artificial Sequence
<220> FEATURE:
<223> OTHER INFORMATION: PCR primer 116 for Ribosome-inactivating
      protein, bouganin.
<220> FEATURE:
<221> NAME/KEY: misc_feature
<222> LOCATION: 3, 6, 12, 15
<223> OTHER INFORMATION: n -continued

```
<400> SEQUENCE: 3
ggngtnccyt tngcnagytc rtt                                              23

<210> SEQ ID NO 4
<211> LENGTH: 20
<212> TYPE: DNA
<213> ORGANISM: Artificial Sequence
<220> FEATURE:
<223> OTHER INFORMATION: PCR primer 102 for Ribosome-inactivating
      protein, bouganin.
<220> FEATURE:
<221> NAME/KEY: misc_feature
<222> LOCATION: 3, 9
<223> OTHER INFORMATION: n = A,T,C or G

<400> SEQUENCE: 4
ggngargcnt aygartaycc                                                  20

<210> SEQ ID NO 5
<211> LENGTH: 65
<212> TYPE: DNA
<213> ORGANISM: Bougainvillaea Spectabilis

<400> SEQUENCE: 5
ggggaggcct acgagtatcc cactttata caagatttgc gcaacgaact cgctaaagga       60
acccc                                                                  65

<210> SEQ ID NO 6
<211> LENGTH: 25
<212> TYPE: DNA
<213> ORGANISM: Artificial Sequence
<220> FEATURE:
<223> OTHER INFORMATION: PCR primer 125 for Ribosome-inactivating
      protein, bouganin.

<400> SEQUENCE: 6
cttttataca agatttgcgc aacga                                            25

<210> SEQ ID NO 7
<211> LENGTH: 20
<212> TYPE: DNA
<213> ORGANISM: Artificial Sequence
<220> FEATURE:
<223> OTHER INFORMATION: PCR primer 197 for Ribosome-inactivating
      protein, bouganin.
<220> FEATURE:
<221> NAME/KEY: misc_feature
<222> LOCATION: 6, 15, 18
<223> OTHER INFORMATION: n = A,T,C or G

<400> SEQUENCE: 7
aaytcnaryt trtancancc                                                  20

<210> SEQ ID NO 8
<211> LENGTH: 363
<212> TYPE: DNA
<213> ORGANISM: Bougainvillaea Spectabilis
<220> FEATURE:
<221> NAME/KEY: CDS
<222> LOCATION: (2)...(361)

<400> SEQUENCE: 8 t ttt ata caa gat ttg cgc aac gaa ttg gct aag ggc aca cca gta tgt     49
  Phe Ile Gln Asp Leu Arg Asn Glu Leu Ala Lys Gly Thr Pro Val Cys
   1               5                  10                  15
```

| | | | | | | | | | | | | | | |
|---|---|---|---|---|---|---|---|---|---|---|---|---|---|---|
| caa | ctt | cca | gtg | aca | cta | caa | acc | ata | gcc | gat | gac | aag | cga | ttt | gtt | 97 |
| Gln | Leu | Pro | Val | Thr | Leu | Gln | Thr | Ile | Ala | Asp | Asp | Lys | Arg | Phe | Val | |
| | | | 20 | | | | | 25 | | | | 30 | | | |

```
cta gtt gat atc act acg acc tcg aag aaa aca gtt aag gtt gct ata    145
Leu Val Asp Ile Thr Thr Thr Ser Lys Lys Thr Val Lys Val Ala Ile
         35                  40                  45 gat gtg aca gat gtg tat gtt gtg ggt tat caa gac aaa tgg gat ggc    193
Asp Val Thr Asp Val Tyr Val Val Gly Tyr Gln Asp Lys Trp Asp Gly
     50                  55                  60 aaa gat cga gct gtt ttc ctt gac aag gtt cct act gtt gca act agt    241
Lys Asp Arg Ala Val Phe Leu Asp Lys Val Pro Thr Val Ala Thr Ser
 65                  70                  75                  80 aaa ctt ttc cca ggg gtg act aat cgt gta acg tta aca ttt gat ggc    289
Lys Leu Phe Pro Gly Val Thr Asn Arg Val Thr Leu Thr Phe Asp Gly
                 85                  90                  95 agc tat cag aaa ctt gtg aat gct gcc aaa gtg gat aga aag gat ctc    337
Ser Tyr Gln Lys Leu Val Asn Ala Ala Lys Val Asp Arg Lys Asp Leu
            100                 105                 110 gaa ctg ggc gtc tac aaa ctc gag tt                                 363
Glu Leu Gly Val Tyr Lys Leu Glu
            115                 120

<210> SEQ ID NO 9
<211> LENGTH: 149
<212> TYPE: PRT
<213> ORGANISM: Bougainvillaea Spectabilis

<400> SEQUENCE: 9

Tyr Asn Thr Val Ser Phe Asn Leu Gly Glu Ala Tyr Glu Tyr Pro Thr
 1               5                  10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
         35                  40                  45

Leu Val Asp Ile Thr Thr Thr Ser Lys Lys Thr Val Lys Val Ala Ile
     50                  55                  60

Asp Val Thr Asp Val Tyr Val Val Gly Tyr Gln Asp Lys Trp Asp Gly
 65                  70                  75                  80

Lys Asp Arg Ala Val Phe Leu Asp Lys Val Pro Thr Val Ala Thr Ser
                 85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Val Asp Arg Lys Asp Leu
        115                 120                 125

Glu Leu Gly Val Tyr Lys Leu Glu Phe Ser Ile Glu Ala Ile Trp Gly
    130                 135                 140

Lys Thr Gln Asn Gly
145
```

TYPE-1 RIBOSOME-INACTIVATING PROTEIN

CROSS REFERENCE TO RELATED APPLICATIONS

This application is a continuation of U.S. patent application Ser. No. 09/445,160, which was filed on Mar. 10, 2000, and issued as U.S. Pat. No. 6,680,296, on Jan. 20, 2002.

FIELD OF THE INVENTION

The invention discloses a new type-1 ribosome-inactivating protein (RIP), referred to as bouganin, isolated from the leaves of *Bougainvillea* species, especially *B. spectabilis* Willd. Bouganin differs from other type-1 RIP by its unique amino acid composition. Bouganin has a molecular weight of about 26,200 daltons. Bouganin is useful as an immunomodulator, anti-viral agent or anti-tumour agent. Compositions comprising bouganin and a cell binding ligand are particularly useful to kill cells of a target population.

BACKGROUND OF THE INVENTION

Ribosome—Inactivating Proteins

It has been known for a long time that extracts from many plant tissues possess anti-viral activity, which in several cases is due to proteins identified as inhibitors of protein synthesis, called ribosome-inactivating proteins (RIP, reviewed by Barbieri et al., *Biochim. Biophys. Acta* 1154:237 (1993)). The pokeweed anti-viral protein (PAP) was the first anti-viral protein to be identified as a RIP (reviewed by Irvin, in *Antiviral Proteins in Higher Plants* 65 (1994)). Subsequently, all other RIP tested possess anti-viral activity not only against plant viruses, but also against animal viruses, including HIV (reviewed by Battelli and Stirpe, in *Antiviral Proteins in Higher Plants* (1994)).

All RIP, either single-chain (type-1) or two-chain (type-2), enzymatically release adenine from a single nucleotide in a precise position ($A_{4324}$ in the case of rat liver 28S rRNA, $A_{2660}$ of *E. coli* rRNA) in a universally conserved GAGA tetraloop of the major rRNA (Endo and Tsurugi, *J. Biol. Chem.* 262:8128 (1987); reviewed by Barbieri et al., *Biochim. Biophys. Acta* 1154:237 (1993)). Depurinated ribosomes become unable to elongate the nascent peptide chain.

The anti-viral activity of these proteins was commonly attributed to the inactivation of ribosomes, with inhibition of protein synthesis of the host cell and consequent arrest of viral replication. However a degradation of supercoiled DNA in the presence of RIP was reported (Li et al., *Nucleic Acid Res.* 22:6309 (1991); Ling et al., *FEBS Lett.* 345:143 (1994); Roncuzzi and Gasperi-Campani, *FEBS Lett.* 392:16 (1996)). Moreover, at least some RIP release more than one adenine residue from ribosomes (Barbieri et al., *Biochem. J.* 286:1 (1992)) and act on RNA species other than ribosomal, including viral RNAs, on poly(A), and on DNA (Barbieri et al, *Nature* 372:624 (1994), *Nucleic Acid Res.* 25:518 (1997); Stirpe et al., *FEBS Lett* 382:309 (1996)). Thus many, if not all, RIP have polynucleotide;adenosinc glycosidase activity, which may have a role in the anti-viral activity besides the inactivation of the host cell ribosomes.

Immunotoxins

Immunotoxins are chimeric molecules in which cell-binding ligands are coupled to toxins or their subunits. The ligand portion of the immunotoxin is usually an antibody that binds to selected target cells. The toxin portion of the immunotoxin can be derived form various sources. Most commonly, toxins are derived from plants or bacteria, but toxins of human origin or synthetic toxins (drugs) have been used as well. Toxins used for immunotoxins derived from plants or bacteria all inhibit protein synthesis of eukaryotic cells, The most widely used plant toxin, ricin, consist of two disulfide-linked polypeptides A and B (Olsncs et al., in *Molecular Action of Toxins and Viruses* 51 (1982)). Another group of plant-derived toxins used in immunotoxins are the type-1 RIP. These molecules are single-chain proteins found in plants and have similar enzymatic properties as the A-chain of ricin (reviewed in Stirpe and Barbieri *FEBS Lett.* 195:1 (1986)).

The cross-linker used to join the ligand (antibody) and the toxin must remain stable when extracellular, but labile when intracellular, so that the toxin fragment can enter the cytosol. The choice of cross-linker depends on whether intact toxins, A-chains or type-1 RIP are used. A-chains and type-1 RIP are generally coupled to the ligand using linkers that introduce a disulfide blind between the ligand and the A-chain (Myers et al., *J. Immunol. Meth.* 136:221 (1991)). Intact toxins are usually linked to ligands using non-reducible linkages (such as thioether) to prevent release of the active free toxin in Vivo. Recombinant immunotoxins have been prepared by splicing the genes encoding the toxin to the gene encoding the ligand (for instance a recombinant antibody fragment) and expressing the entire immunotoxin as a fusion protein (Pastan et al, *Ann, Rev. Biochem.* 61:331 (1992)). Recombinant immunotoxins are highly stable in vivo because they contain non-reducible peptide bonds.

Various types of immunotoxins directed against different cellular targets have been evaluated in vivo, both in animal models and in phase I or II clinical trials. The results of a number of these studies are reviewed in Ghetie and Vitetta *Curr. Opin. Immunol.* 6:707 (1994) and Thrush et al., *Ann. Rev. Immunol.* 14:49 (1996).

SUMMARY OF THE INVENTION

Ribosome inactivating proteins (RIP) comprise a class of proteins with potent inhibitory activity of eukaryotic protein synthesis. RIP can be classified in two groups. Type-1 RIP consist of a single peptide chain having ribosome inactivating activity, whereas type-2 RIP consist of an A chain with ribosome inactivating activity and a B chain having cell binding activity. Here we describe the isolation of a novel type-1 RIP, referred to as bouganin, with a low non-specific toxicity, making it very suitable for the incorporation as the toxin part in various immunotoxin molecules. The invention pertains to this novel protein and biologically active peptide parts and equivalents thereof, to immunotoxins based on this protein, to the production of such proteins and immunotoxins, and to their use in the medical and plant-protection fields. The invention is defined in the appending claims.

DETAILED DESCRIPTION OF THE INVENTION

The invention described herein draws on previously published work. By way of example, such work consists of scientific papers, parents and pending patent applications. All of these publications and applications, cited previously or below, are hereby incorporated by reference.

The protein according to the invention corresponds to the bouganin protein as described below in more detail, as well as to biologically active fragments and equivalents thereof. The term "biologically active" means being capable of inhibiting protein synthesis in vitro or in viva, Such fragments generally comprise one or more active sites of the protein or the encoding polynucleotide and generally comprise a sequence at least 8 amino acids, preferably at least 10, at least 15 or even at least 30 amino acids of the protein, or the corresponding number of nucleotides of the polynucleotide.

The term "ligand" refers to any molecule capable of binding with or otherwiserecognizing a receptor on a target cell. The ligand may molecule. Examples of such ligands include, but are not limited to, antibodies, growth factors, cytokines, hormones and the like, that specifically bind desired target cells.

As used herein, the term "immunotoxin" refers to chimeric molecules in which a cell binding ligand is coupled to the novel type-1 RIP bouganin or fragments thereof.

As used herein, the term "antibody" refers to polyclonal antibodies, monoclonal antibodies, humanized antibodies, single-chain antibodies, and fragments thereof such as Fab, F(ab')2, Fv, and other fragments which retain the antigen binding function of the parent antibody.

As used herein, the term "monoclonal antibody" refers to an antibody composition having a homogeneous antibody population. The term is not limited regarding the species or source of the antibody, nor is it intended to be limited by the inner in which it is made. The term encompasses whole immunoglobulins as well as fragments such as Fab, F(ab')2, Fv, and others which retain the antigen binding function of the antibody. Monoclonal antibodies of any mammalian species can be used in this invention. In practice, however, the antibodies will typically be of rat or murinc origin because of the availability of rat or murinc cell lines for use in making the required hybrid cell lines or hybridomas to produce monoclonal antibodies.

As used herein, the term "humanized antibodies" means that at least a portion of the framework regions of an immunoglobulin are derived from human immunoglobulin sequences.

As used herein, the term "single chain antibodies" refer to antibodies prepared by determining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al. Methods for the generation of antibodies suitable for use in the present invention are well known to those skilled in the art and can be found described in such publications as Harlow and Lane, *Antibodies: A Laboratory Manual,* Cold Spring Harbor Laboratory, (1988).

The natural or recombinant type-1 RIP bouganin molecules of the present invention may be fused to, or otherwise bound to a ligand by any method known and available to those skilled in the art. The ligand and the bouganin molecules may be chemically bonded together by any of a variety of well-known chemical procedures, such as the use of hetero-bifunctional cross-linkers, e.g. SPDP, 2-iminothiolane, carbodiimide or glutaraldehyde. Production of various immunotoxins is well-known within the art and can be found, for example in Thorpe et al., *Monoclonal Antibody-Toxin Conjugates: Aiming the Magic Bullet* 168 (1982) and Waldmann, *Science,* 252:1657 (1991), both of which are incorporated by reference.

Bouganin may also be fused to the ligand by recombinant means such as through the production of single chain antibodies. The genes encoding ligand and bouganin may be cloned in cDNA form and linked directly or separated by a small peptide linker by any cloning procedure known to those skilled in the art. See for example Sambrook et al., *Molecular Cloning: A Laboratory Manual,* Cold Spring Harbor laboratory, (1989).

A person skilled in the art will appreciate that additional modifications, deletions and insertions may be made to the ligand binding agent and bouganin genes. Especially, deletions or changes may be made in the linker connecting an antibody gene to bouganin. All such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

Fusion proteins of the present invention including bouganin molecules may be expressed in a variety of host cells, including but not limited to bacterial hosts and yeast. The recombinant antibody-bouganin fusion protein gene will be linked to appropriate expression control sequences for each host. For *E. coli* this includes a promoter such as the T7, trp, or lambda promoters, a ribosome binding site and preferably a transcription termination signal. The plasmids of the invention can be transferred into the chosen host cell by well-known methods such as calcium chloride transformation. Cells transformed by the plasmids can be selected by resistance to antibiotics conferred by genes contained on the plasmids, such as, but not limited to, the ampiciline and neomycin genes.

Once expressed, the recombinant antibody-bouganin fusion proteins can be purified according to standard procedures of the art, such as described in R. Scopes, *Protein Purification,* Springer Verlag, N.Y. (1982), Substantially pure compositions of at least about 90 to 95% homogeneity are for pharmaceutical uses. Once purified, partially or to homogeneity as desired, the polypeptides may then be used therapeutically.

The pharmaceutical compositions of this invention are administered at a concentration that is therapeutically effective to a patient in the need of a treatment. To accomplish this goal, the pharmaceutical compositions may be formulated using a variety of acceptable excipients known in the art. The compositions for administration will commonly comprise a solution of the bouganin molecule, antibody-bouganin conjugates, single chain antibody-bouganin fusion proteins, ligand-bouganin conjugates or single chain ligand-bouganin fusion proteins dissolved in a pharmaceutically acceptable carrier, preferably an aqueous carrier. Typically, the compositions are administered by injection, either intravenously, intraperitoneally, in an other body cavity or into a lumen of an organ. Methods to accomplish this administration are known to those of ordinary skill in the art. It may also be possible to obtain compositions which may be topically or orally administered, or which may be capable of transmission across mucous membranes.

The pharmaceutical compositions may also contain a polynucleotide encoding the bouganin molecule or active parts thereof, for use in gene therapy. The polynucleotide may be combined with means for specific delivery of the polynuclcotide at the site were cells are to be killed by incorporation of the polynucleotide; such targeting means may e.g. be site-specific antibodies, liposomes or other art-known targeting devices.

Before administration to patients, formulants may be added to the antibodies. A liquid formulation is preferred, For example, these formulants may include oils, polymers, vitamins, carbohydrates, amino acids, salts, buffers, albumin, surfactants, or bulking agents. Preferably carbohydrates include sugar or sugar alcohols such as mono-, di-, or polysaccharides. The saccharides can include fructose, glucose, mannose, sorbose, xylose, lactose, maltose, sucrose, dextran, pullulan, dextran, α- and β-cyclodextrin, soluble starch, hydroxyethyl starch, carboxymethyl cellulose, other water-soluble glucans, or mixtures thereof. Sucrose is most preferred. "Sugar alcohol" is defined as a $C_4$ to $C_8$ hydrocarbon having OH groups, and includes galactitol, inositol, mannitol, xylitol, sorbitol, glycerol, and arabitol. Mannitol is most preferred. These sugars or sugar alcohols mentioned above may be used individually or in combination. There is no fixed limit to the amount used, as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginilie, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Any physiologically acceptable buffer may be used, but citrate, phosphate, succinate, and glutamate buffers or mixtures thereof are preferred. Most preferred is a citrate buffer. Preferably, the concentration is from 0.01 to 0.3 M. Surfactants can be a added to the formulation, for example those shown in EP-A-270799 and EP-A-268110.

Additionally, antibody-bouganin conjugates or single chain antibody-bouganin fusion proteins can, for example, be chemically modified by covalent conjugation to a polymer to increase their circulating half-life. Preferred polymers, and methods to attach them to peptides, are shown in U.S. Pat. Nos. 4,166,106, 4,179,337, 4,495,285 and 4,609,546, which are all hereby incorporated by reference in their entireties. Preferred polymers are polyoxyethylated polyols and polyethylene glycol (PEG). PEG is soluble in water at room temperature and has the general formula: $R(O-CH_2-CH_2)_n O-R$ where R can be hydrogen, or a protective group such as an alkyl or alkanol group. Preferably, the protective group has between 1 and 8 carbons, more preferably it is methyl. The symbol a is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf er al, *J. Biol. Chem.* 263:15064 (1988), and a discussion of POG/IL-2 conjugates is found in U.S. Pat. No. 4,766,106, both of which are hereby incorporated by reference in their entireties.

Another drug delivery system for increasing circulatory half-life is the liposome. Methods of preparing liposome delivery systems are discussed in Gabizon et al., *Cancer Res.* 42:4734 (1982); Cafiso, *Biochim. Biophys. Acta* 649:129 (1981); and Szoka, *Ann. Rev. Biophys. Eng.* 9:467 (1980). Other drug delivery systems are known in the art and are described in e.g., Poznansky et al., *Drug Delivery Systems* 253 (1980); Poznansky, *Pharm. Rev.* 36:277 (1984).

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art. As stated above, the compositions of this invention are especially used to treat human patients. The preferred route of administraxtrose in saline. The vehicle may contain minor amounts of additives such as substances that enhance isotonicity and chemical stability, including buffers and preservatives.

The dosage and mode of administration will depend on the individual. Generally, the compositions are administered so that antibodies are given at a dose between 1 μg/kg and 20 mg/kg, more preferably between 20 μg/kg and 10 mg/kg. Preferably, it is given as a bolus. Continuous infusion may also be used, if so, the compositions may be infused at a dose between 1 and 100 μg/kg/min.

The compositions containing the present pharmaceutical compositions or a cocktail thereof (i.e., with other pharmaceutically active proteins) can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the pharmaceutical compositions of the present invention are included a variety of disease conditions caused by specific human cells that may be eliminated by the toxic action of the protein. One preferred application is the treatment of cancer, such as by the use of a tumour cell binding antibody as the ligand or of autoimmune conditions such as graft-versus-host disease, organ transplant rejection, type I diabetes, multiple sclerosis, rheumatoid arthritis, systemic lupus erythematosus, myasthenia gravis and the like. The pharmaceutical compositions may also be used in vitro, for example, in the elimination of harmful cells from bone marrow before transplant. The ligand portion of bouganin containing conjugates and fusion proteins is chosen according to the intended use. A large number of cell membrane molecules on lymphocytes may serve as target of the ligand part of the immunotoxin. Also antigens found on cancer cells that may serve as targets for the ligand part of immunotoxin with bouganin. Those skilled in the art will understand that ligands may be chosen that bind to receptors expressed on other types of cells as well.

The bouganin molecule itself has also applications as an anti-viral compound. Type-1 RIP are know to be active against viruses affecting mammals and plants. Bouganin can therefore be used as a therapeutic molecule to treat viruses.

The discovery of the anti-viral activity of RIP against a broad range of plant viruses when applied exogenous to inoculated leaves, has led to transfection of genes coding for RIP in host plants. Virus infection modifies the permeability of the cell membrane, thereby allowing the access of normally excluded molecules to the cytoplasm. RIP can then enter the virus infected cell and, once inside, inactivate ribosomes and viral replication. Besides the anti-viral activity of RIP, transfection of genes coding for RIP in host plant can also be applied to insect pest control. RIP are only moderately inhibitory for plant ribosomes but are highly inhibitory for ribosomes of plant parasites and are consequently good candidates for parasite control in plants. Transformation of an economically important host plant with the gene for a RIP which is toxic to parasites and is ineffective on the ribosomes of the plant confers specific resistance, An example of such a transgenic plant is a tobacco plant transfected with the Barley RIP. The constitutive expression of RIP in host plant can cause abnormal development of transgenic plant that can limit their application. To circumvent this problem a virus induced expression of RIP in transgenic plant is used, affecting only virus-infected cells without causing abnormal developing plants. Purified bouganin can also be applied directly in small amount on the leaves, completely preventing the mechanical transmission of unrelated viruses to several different host plants (Chen et al., *Plant Pathol.* 40;612 (1991)).

The present invention will now be illustrated by reference to the following examples which set forth particularly advantageous embodiments. However, it should be noted that these embodiments are illustrative and are not to be construed as restricting the invention in any way.

DESCRIPTION OF THE FIGURES

FIG. 2 shows the specificity of the polyclonal anti-bouganin serum in an ELISA experiment when bouganin was coated to the plates FIG. 3 shows a comparison of the N-terminal amino acid sequence of bouganin with a number of other type-1 RIP. Bouganin (SEQ ID No. 1), gelonin (SEQ ID No. 10). momorcharin (SEQ ID No. 11), trichosanthin (SEQ ID No. 12), MAP (SEQ ID No. 13), saporin (SEQ ID No. 14), bryodin2 (SEQ ID No. 15). bryodini 1 (SEQ ID No. 16), ricin A (SEQ ID No. 17), luffin A(SEQ ID No. 18), mormordin (SEQ ID No. 19), PAPS (SEQ ID No. 20), dodecandrin (SEQ ID No. 21), B. rubra RIP 2 (SEQ ID No. 22), B. rubra RIP 3 (SEQ ID No. 23), BRIP (SEQ ID No. 24). Amino acids are denoted by the single letter code.

FIG. 4 shows the toxic activity of the bouganin immunotoxins based on anti-CD80 and anti-CD86 monoclonal antibodies (Mabs) when tested on CD80 and CD86 positive Raji cells. Toxic activity was evaluated from the inhibition of protein synthesis by the Raji cells.

FIG. 5 shows the toxic activity of the bouganin immunotoxins based on anti-CD80 and anti-CDB6 monoclonal antibodies (Mabs) when tested on CD80 and CD86 positive LA28 cells. Toxic activity was evaluated from the inhibition of protein synthesis by the LA28 cells.

FIG. 7 shows the clonogenicity of the Raji and L248 cell lines after short term exposure to the immunotoxins.

EXAMPLES

Example 1

Purification of Bouganin, a Novel Type-1 RIP from the Leaves of *Bougainvillea Spectabilis* Willd For the purification of the novel type-1 RIP, the following purification scheme was used. During the purification procedure, RIP activity was monitored using a rabbit reticulocyte lysate assay as described (Parente et al., *Biochim Biophys. Acia* 1216.43 (1993)). Reaction mixtures contained 10 mM Tris/HCl buffer, pH 7.4, 100 mM ammonium acetate, 2 mM magnesium acetate, 1 mM ATP, 0.2 mM GTP, 15 mM phosphocreatine, 3 µg of creatine kinase, 0.05 mM amino acids (minus leucine), 89 nCi of L-[$^{14}$C]-leucine, and 25 µl of rabbit reticulocyte lysate in a final volume of 62.5 µl. Incubation was at 28° C. for 5 min. Protein concentration in the different purification steps was determined by spectrophotometry (Kalb et al. *Anal. Biochem.* 82:362 (1977)).

Figure 1:
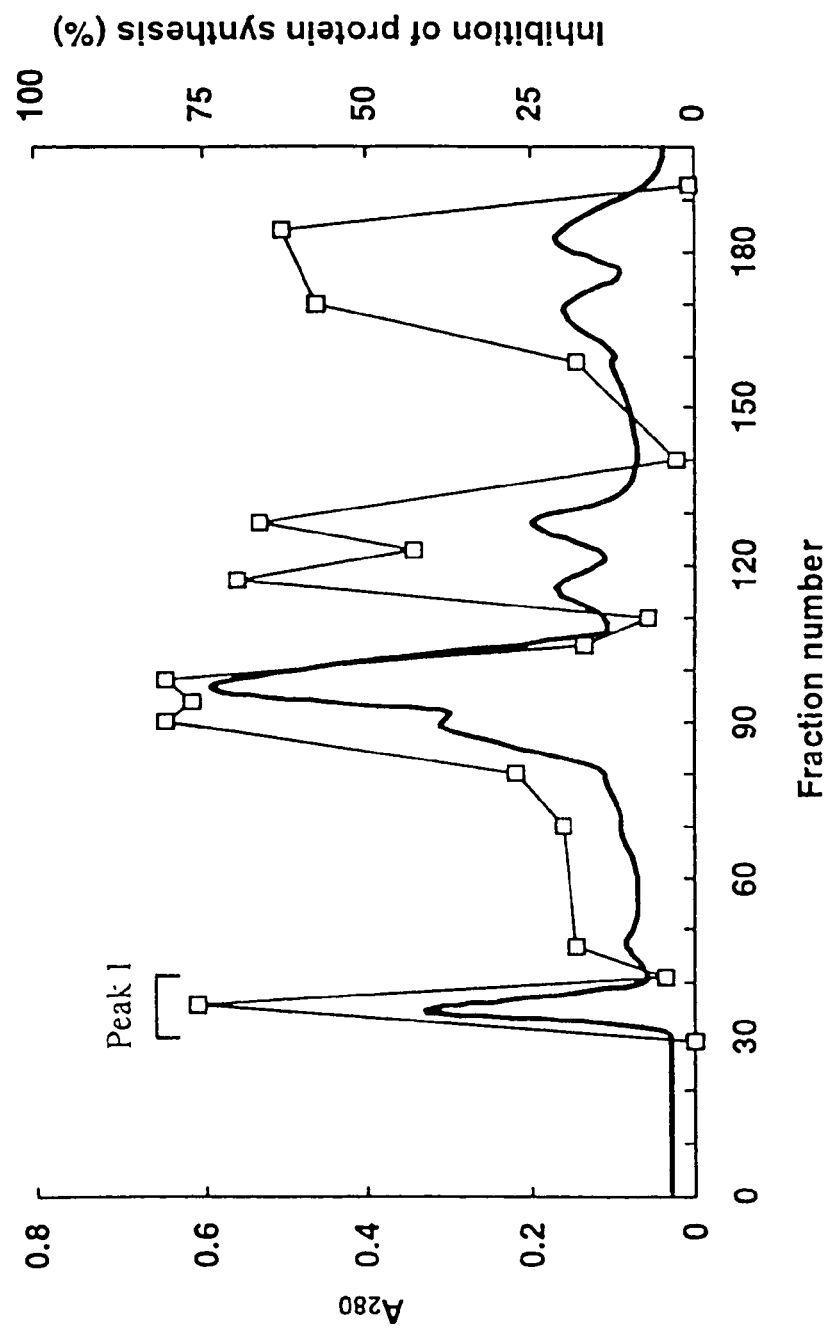
FIG. 1 shows the elution profile of this column step (solid line) in relation to the activity in the rabbit reticulocyte lysate assay (open circles). It can be seen that the activity in the rabbit reticulocyte lysate assay was resolved in several protein peaks.

*B. spectabilis* leaves were obtained from the Botanic Garden of the University of Bologna (Italy). *B. spectabilis* leaves (1,400 gram) were ground in a mortar with liquid nitrogen and homogenized with an Ultraturrax apparatus in PBS (4 ml/g leaves). The slurry was extracted overnight at 4° C. with magnetic stirring, filtered through cheesecloth, adjusted to pH 4.0 with glacial acetic acid, and centrifuged (10,000×g) for 30 min. at 4° C. The acidified extract was applied to an S-Sepharose Fast Flow column (12×18 cm) equilibrated with 10 mM sodium acetate, pH 4.5. The column was extensively washed with 5 mM sodium phosphate buffer, pH 7.0, and bound protein was eluted with 1 M NaCl in the same buffer. Active fractions were pooled and protein was precipitated by the addition of ammonium sulfate to saturation at 4° C. The precipitated material was recovered by centrifugation (10,000×g) for 30 min. at 4° C. The pellet was dissolved and dialysed against water at 4° C., then clarified by centrifugation at (10,000×g) for 30 min. at 4° C. The supernatant was adjusted to 5 mM phosphate buffer, pH 7.5, and applied to a CM-Sepharose Fast Flow column (30×1.6 cm) in the same buffer. The column was washed with the equilibration buffer and eluted with a NaCl linear gradient (from 0 to 200 mM in the same buffer, total volume 800 ml). FIG. 1 shows the elution profile of this column step (solid line) in relation to the activity in the rabbit reticulocyte lysate assay (open circles). It can be seen that the activity in the rabbit reticulocyte lysate assay was resolved in several protein peaks. The protein peak denoted in FIG. 1 as Peak 1 was analysed using reverse phase HPLC on a Vidac C4 column as described previously (Parente et at., *Biochim. Biophys. Acta* 1216:43 (1993)) and gave only one single peak. It was therefore concluded that the activity was from a single protein. Table 1 summarizes the results of all the purification steps.

TABLE 1

Purification of RIP from leaves of *Bougainvillea spectabilis* Willd[a]

| Preparation | Total protein (mg) | IC$_{50}$ activity[b] (ng/ml) | Specific activity[c] (10$^3$ U/mg) | Total activity (10$^6$ U) | Yield (%) |
|---|---|---|---|---|---|
| acidified extract | 3454 | 871 | 1.15 | 3.97 | 100 |
| S-Sepharose eluate | 300 | 100 | 10 | 3 | 75 |

TABLE 1-continued

Purification of RIP from leaves
of *Bougainvillea spectabilis* Willd[a]

| Preparation | Total protein (mg) | IC$_{50}$ activity[b] (ng/ml) | Specific activity[c] (10$^3$ U/mg) | Total activity (10$^6$ U) | Yield (%) |
|---|---|---|---|---|---|
| CM-sepharose eluate | | | | | |
| peak-1 | 3.5 | 10.5 | 95.5 | 0.33 | 8 |
| other active peaks | 26.3 | — | — | 0.99 | 25 |

[a]results refer to 100 g of starting material
[b]IC$_{50}$ is the protein amount that inhibits synthesis by 50% in a rabbit reticulocyte lysate system
[c]One unit (U) is the protein amount causing 50% inhibition of cell-free protein synthesis in 1 ml Example 2

Characterization of Bouganin

The purified protein peak 1 of example 1 was subjected to SDS-PAGE gel electrophoresis and analysed with a Epson GT8000 densitometer, utilizing a Gel Image program (Pharmacia, Sweden), This analysis showed a single band of 26.2 kDa. The pI of the purified protein peak 1 was 9.0 (determined with a Phast System (Pharmacia) with the gels provided by the manufacturer). The absorption of the purified RIP from peak 1 was 8.72 (absorption was determined with water solutions of freeze-dried samples). The purified RIP from protein peak 1 is referred to as bouganin.

In order to obtain a polyclonal anti-bouganin serum for detection purposes, the isolated protein has been used for immunization of rabbits. The animals were immunized with 250 μg of isolated protein in a total volume of 1 ml containing 0.5 ml of the protein dissolved in PBS and 0.5 ml of complete Freund's adjuvant, by multi-site intradermic administration on day 0. Subsequent booster injections, also by multi-site intradermic administration, were given at day 14, 28 and 56 with the same amount of bouganin but now using Freund's incomplete adjuvant. Preimmune serum was taken followed by test bleedings on day 38 and 66. Animal were sacrificed on day 80 and a large batch of polyclonal anti-bouganin serum was obtained. The polyclonal anti-bouganin serum is able to bind specifically to bouganin in ELISA (FIG. 2), when bouganin was coated to the ELISA plates, and in Western blot analysis.

Example 3

Partial Amino Acid Sequencing of Bouganin

The N-terminal amino acid sequence of bouganin was determined by the method described by Parente et al., *Biochim. Biophys. Acta* 1216:43 (1993). The N-terminal amino acid sequence of bouganin is shown below.

Bouganin (SEQ ID NO:1)

YNTVSFNLGEAYEYPTFIQDLRNELAKGTP

The N-terminal amino acid sequence of bouganin was compared to know protein sequences using the BLAST search method of the National Center for Biotechnology Information (NCBI) (Altschul et al., *J. Mol. Biol.* 215;403 (1990)). This protein data base search revealed that bouganin does not match with any known protein sequence. It can be seen in FIG. 3 that bouganin has only limited homology to other known type-1 RIP. The amino acid identity of bouganin with known type-1 RIP ranged from 20% to 37% and was clearly confined to a number of conserved amino acid residues.

Internal amino acid sequence data were obtained by digesting the isolated bouganin protein using VB protease. The proteolytic generated peptide fragments were analysed using SDS-PAGE electroforesis and subsequently electroblotted to a poly-vinylidene difluoride (PVDF) membrane, Using Edman Degradation for amino acid sequencing, one internal amino acid sequence was revealed. This sequence is as follows:

Bouganin (SEQ ID NO:1)

(E)LGVYKLEFSIEAI(W)GKTQNG

The amino acids placed between brackets in the obtained sequence are uncertain.

Example 4

Biological Characterization of Bouganin

From Table 1 above, it was calculated that bouganin inhibits protein synthesis in the rabbit reticulocyte lysate assay with an IC$_{50}$ of $4.01 \times 10^{-11}$ M. Bouganin was also tested for the inhibition of protein synthesis of various human cell lines. The cell lines used, namely mouse 3T3(fibroblasts), and human HeLa (carcinoma), NB100 (neuro-blastoma) and BeWo (chorion carcinoma) were maintained as monolayer cultures in RPMI 1640 medium supplemented with antibiotics and 10% fetal calf serum, in a humidified atmosphere containing 5% $CO_2$, at 37° C. Subcultures were obtained by trypsin treatment of confluent cultures. The human JM cell line (monocyte-derived) was grown in suspension and treated with phorbot myristate acetate to induce adhesion as described (Bolognesi et al., *Eur. J. Biochem.* 228:935 (1995)). Protein synthesis by various cell lines was assayed as described previously (Ferreras et al., *Biochim. Biophys. Acta* 1216. 31 (1993)). Cells (10$^5$/well) were incubated with bouganin for 18 h., followed by a 2 h. pulse with L-[4,5-$^3$H] leucine (125 nCi/0.25 ml, obtained from Amersham International, Bucks., UK). The IC$_{50}$ (concentration giving 50% inhibition) was calculated by linear regression analysis. Table 2 sows that the bouganin concentrations needed to inhibit protein synthesis of these human cell lines were much higher than the concentration needed to inhibit the protein synthesis in the rabbit reticulocyte lysate assay. This indicates that the cells tested do not have specific receptors to internalize bouganin.

Bouganin was also tested for its capacity to release adenine from various sources. Poly(A) and rRNA from *Escherichia coli* (16S +23S, m.wt. $1.75 \times 10^6$) were from Boebringer GmbH, Mannheim, Del. DNA from hearing sperm (Sigma Chemical Co., St. Louis, Mo., USA) was mechanically sheared and -made RNA-free by treatment with DNase-free RNase A (Boehringer GmbH, Mannheim, Del.) for 2.5 h. at 37° DNA was then repeatedly precipitated in ethanol to remove the enzyme. Genomic RNA (mn ssRNA positive+one small satellite, m.wt. $1.49 \times 10^6$) from artichoke mottled crinkle virus (AMCV) was prepared by phenol extraction and ethanol precipitation from purified virus isolates. Rat liver ribosomes were prepared essentially as described elsewhere (Arias et al., *Planta* 186:532 (1992)) in RNase-free conditions. Their concentration was determined by the A$_{260}$ according to Montanaro et al. *Biochem. J.* 176:371 (1978), assuming that 12.5 AU/ml were equivalent to 1 mg/ml and that 1 mg contained 250 pmol of ribosomes. Ribosomes were stored in aliquots at −80° C.

TABLE 2

Effect of *B. Spectabilis* RIP on protein synthesis by cell lines[a]

| Cell line | Origin | Incorporation of [$^3$H] leucine by control cells(dpm ± SD) | Inhibition of protein synthesis (IC$_{50}$[b]) (ng/ml) |
|---|---|---|---|
| JM | monocytes | 8555 ± 824 | 1218 ± 484 |
| HeLa | carcinoma | 24082 ± 6367 | >3300 |
| NB100 | neuroblastoma | 12607 ± 3694 | 665 ± 0 |
| BeWo | chorion carcinoma | 18995 ± 7332 | 950 ± 16 |
| 3T3 | fibroblasts | 4317 ± 2652 | >3300 |

[a]Results are mean values ± S. D. of two experiments performed in triplicate.
[b]IC$_{50}$: concentration of protein inhibiting protein by 50% as compared to controls.

Determination of polynucleotide adenosinc glycosidase activity was determined by measuring adenine (obtained from Sigma Chemical Co., St. Louis, Mo., USA) released from the various sources by HPLC (Zamboni et al., *Biochem. J.* 259:639 (1989)), essentially following the procedure of McCann et al, *Antimicrob. Agents Chernother.* 28:265 (1985) as described by Stirpe et al. *FEBS Lett.* 382:309 (1996). Reactions were run for 40 min, at 30° C. in a final volume of 50 µl containing 50 mM sodium acetate, pH 4.0, 100 mM KCl, bouganin and substrate. Controls were run without bouganin, and a standard curve of adenine was run with each experiment. Bouganin not only released adenine from rat liver ribosomes (One mole of adenine per ribosome, approximately), but also from *E. coli* rRNA, from poly(A), from genomic AMCV RNA and from herring sperm DNA. Among polynucleotides, DNA appeared the best substrate. The number of adenine residues released was near to one per ribosome, and several per mol of rRNA or AMCV RNA.

Example 5

In Vivo Toxicity of Bouganin

Bouganin was also tested for toxicity in animals. Various doses were injected i.p. to groups of three male and three female Swiss mice. The ratio between doses was two, and the animals were observed up to 16 days after treatment. Other known RIP have a toxicity (LD$_{50}$ values) in the range of 1 to 40 mg/kg (Barbieri et al., *Biochim Biophys. Acta* 1154:237 (1993)). Bouganin was not toxic in the test animals at a dose as high as 32 mg/kg.

Example 6

Generation of Chemically Coupled Anti-CD80 and Anti-CD86 Immunotoxin Molecules Containing Bouganin Immunotoxins containing bouganin were prepared essentially according to the method described by Bolognesi et al. *Clin. Exp. Immunol.* 89;341 (1992). Anti-CD80 (Mab B7-24), anti-CD86 (Mab 1G10) and bouganin, the latter containing a trace of $^{125}$I-RIP, were dissolved in 50 mM sodium borate buffer, pH 9.0, at a concentration of 1 mg/ml, 1.5 mg/ml and 2.5 mg/ml, respectively, and were modified by adding 2-imino-thiolane (Sigma) to a final concentration of 0.6 mM (Mab), 1.0 mM (bouganin). After 60 min. at room temperature (21° C.), glycine was added to a final concentration of 200 mM, and after further 20 min. Ellman's reagent, dissolved in 50 Fl of dimethylformamide, was added to a final concentration of 2.5 mM. After 10 min. at room temperature the reaction mixture was filtered through a Sephadex G25 column, and the number of sulphydryl groups introduced was determined. The derivatised RIP were reduced with 20 mM 2-mercaptoethanol, filtered through a Sephadex G25 column, and were then mixed with the modified Mab in a RIP:Mab ratio 10:1. After 18 h. at room temperature the conjugates were separated from the unreacted reagents by gel filtration on a Sephacryl S200 high-resolution column, equilibrated and eluted with phosphate buffered saline (PBS, 0.14 M NaCl in 5 mM sodium phosphate buffer, pH 7.4). Protein synthesis inhibitory activity of the fractions was assayed on a rabbit reticulocyte lysate as described (Bolognesi er al., *Eur. J. Biochem.* 228:935 (1995)).

The RIP:Mab ratio in the conjugates was estimated from the $^{125}$I-RIP radio-activity and from the protein concentration calculated from the $A_{280}$. The conjugates were sterilized by filtering through a 0.22 µm filter and stored at 4° C. at concentration higher than $10^{-6}$ M.

Example 7

Characterization of Chemically Coupled Anti-CD80 and Anti-CD86 Immunotoxin Molecules Containing Bouganin The activity of the bouganin containing conjugates in comparison to the activity of gelonin and saporin containing conjugates coupled to anti-CD80 and anti-CD86 Mabs, was assayed on the Raji cell line, derived from a Burkitt lymphorna, and the LA28 cell line, derived from a Hodgkin's lymphoma. Cells were maintained in RPMI 1640 medium with 10% fetal bovine serum (FBS) (Gibco), glutamine (Sigma) and antibiotics (Bio-whittaker). The type 1 RIPs gelonin and saporin (saporin-S6), were purified as previously described by Barbieri et al. *J. Chromatography* 408:235 (1987) from the seeds of Gelonium multiflorum and Saponaria officials, respectively, subsequently anti-CD80 and anti-CD86 immunotoxins were prepared containing gelonin and saporin as was described above for the bouganin containing immunotoxins.

Before each series of experiments the reactivity of the target cells with anti-CD80 and anti-CD86 Mabs was ascertained by means of immunofluorescence and flow cytomtry. Briefly, cells, harvested and checked for viability by trypan blue dye exclusion, were adjusted to a concentration of $10^6$ cells/ml of complete RPMI 1640 medium. To 100 µl of cell suspension, 100 µl of a $10^{-7}$ M solution of the Mabs were added. Negative samples were run with appropriate isotype-matched irrelevant Mab. Cells were incubated for 30 min. at 4° C., washed twice in phosphate-buffered saline containing 1% FBS, and incubated again in a volume of 50 µl with 4 µl of FITC-GAM. After three washings with PBS containing 1% FBS the samples were fixed with PBS containing 1% formalin. Binding of Mabs was assessed by flow cytometry, with an EPICS XL equipment (Coulter). Histograms and statistics were generated with the software of the EPICS-dedicated computer. Both cell lines were found to be positive for expression of both CD80 and CD86.

The inhibitory activity of immunotoxins on cell-free protein synthesis was evaluated with a rabbit reticulocyte lysate. Immunotoxins were prior reduced with 20 mM 2-mercaptoethanol for 30 min. at 37° C., appropriately diluted and then added to a reaction mixture containing, in a final volume of 62.5 µl: 10 mM Tris/HCl buffer, pH 7.4, 100 mM ammonium acetate, 2 mM magnesium acetate, 1 mM ATP, 0.2 mM GTP, 15 mM phosphocreatine, 3 µg of creatine kinase, 0.05 mM amino acids (minus leucine), 3.3 kBq of L-$^{14}$C-leucine (Amersham International, Bucks, UK) and 25 µl of a rabbit reticulocyte lysate. Incubation was at 28° C. for 5 min. The reaction was arrested with 1 ml of 0.1 M potassium hydroxide, and two drops of hydrogen peroxide and 1 ml of 20% (w/v) of trichloroacetic acid were added. Precipitated proteins were collected on glass-fibre discs and the radioactivity incorporated was measured with a β-counter (Beckman), after the addition of 5 ml of Ready Gel scintillation cocktail (Beckman) containing 0.7% acetic acid. Each experiment was carried out in duplicate. The concentration of immunotoxins, expressed as RIP content, causing 50% inhibition of leucine incorporation ($IC_{50}$) was calculated by linear regression analysis. Table 3 shows the key characteristics of the immunotoxins used.

centrations of immunotoxins (from $10^{-11}$ to $10^{-8}$ M, of the RIP). After 48 h of incubation, L-[4,5-$^3$H]leucine (74 kBq) was added in 100 µl volume of RPMI, and after further 18 h cells were fixed by adding 1 ml of 20% trichloroacetic acid. After three washes with 5% trichloroacetic acid, cells were lysed with 250 µl of 0.1 M potassium hydroxide, for 10 min. at 37° C. The radioactivity was measured as described above. Each experiment was run in triplicate. Results are expressed as the mean of three different experiments, with a SD≦10%.

TABLE 3

Characteristics of the derivatized Mabs and RIPs and of the immunotoxins

| | Mab | | RIP | | | Immunotoxin* | |
|---|---|---|---|---|---|---|---|
| | 2-IT (mM) | Thiol groups inserted (mol/mol) | 2-IT (mM) | Thiol groups inserted (mol/mol) | $IC_{50}$* (ng/ml) | RIP/Mab (mol/mol) | $IC_{50}$* (ng/ml) |
| anti-CD80-bouganin | 0.6 | 2.28 | 1.0 | 0.88 | 16.2 | 3.07 | 22.7 |
| anti-CD80-gelonin | 0.6 | 2.83 | 1.0 | 1.06 | 20.9 | 3.67 | 29.8 |
| anti-CD80-saporin | 0.6 | 2.54 | 1.0 | 1.41 | 2.6 | 2.11 | 7.6 |
| anti-CD86-bouganin | 0.6 | 1.28 | 1.0 | 0.65 | 16.2 | 2.66 | 27.7 |
| anti-CD86-gelonin | 0.6 | 3.01 | 1.0 | 0.74 | 20.9 | 2.73 | 50.1 |
| anti-CD86-saporin | 0.6 | 2.61 | 1.0 | 1.32 | 2.6 | 2.41 | 5.8 |

*expressed as concentration of the RIP.

Six different immunotoxins were obtained with the anti-CD80 and anti-CD86 monoclonal antibodies and three different single chain RIPs (bouganin, gelonin, and saporin). The RIPs were conjugated to the Mabs by an artificial disulfide bond. Sulphydryl groups were inserted in each type of molecule by an immodest reaction between 2-iminothiolane and the primary amino-groups of the proteins. Both Mobs showed a marked reactivity with 2-iminothiolane, with an average of more than 2.5 SH groups inserted per molecule, using a standard concentration of the linking reagent. The three RIPs were less reactive, and amongst them bouganin showed the lower, and saporin the highest, derivatisation grade. After conjugation the toxin/Mab molar ratio resulted of about 2.5 or the anti-CD86 containing immunotoxins, whilst those containing the anti-CD80 Mab gave more variable products, with the toxin/Mab molar ratios ranging from 2.11 to 3.67. The inhibitory activity of native and conjugated RIPs on protein synthesis by a rabbit reticulocyte lysate is also reported in Table 3, A loss of activity on conjugation was observed with all RIPs. This partial inactivation was minimal for saporin and was the greatest in the case of gelonin.

The cytotoxicity of the immunotoxins Was evaluated from the inhibition of $^3$H-leucine incorporation in CD80/86 positive cell lines. Raji and LA28 cells were harvested, checked for viability and adjusted to a concentration of $10^5$ cells/ml in complete RPMI 1640 medium. Cells ($10^4$) were seeded in 96-wells microtiter plates in a volume of 200 µl containing anti-CD80 immunotoxins, or anti-CD86 immunotoxins, or a mixture of the two immunotoxins in concentrations ranging from $10^{-13}$ M to $10^{-8}$ M, of the RIP. Control samples were run with the respective RIP alone, the Mabs alone or a mixture of the Mabs and the free RIPs. In these experiments Ber-H2/saporin and B-B10/saporin were used as irrelevant immunotoxins for Raji and L428 cells, respectively. After 72 h. 74 kBq of $^3$H-leucine (Amersham) was added. After another 18 h. cells were harvested with an automatic cell harvester (Skatron Instruments, Lier, Norway) onto glass-fiber diskettes. The radioactivity incorporated was determined as described above. The 24 cells were trypsinized and seeded in 24 well plates ($2 \times 10^4$ cells/well in 0.5 ml), and used as control cells being CD80 and CD86 negative. After 24 h. the medium was removed and changed with medium containing various con- All tested immunotoxins inhibited $^3$H-leucine incorporation by Raji and L428 cell lines (FIG. 4 and 5). RIPs incremented their toxicity on Raji cells by 3-4 log upon conjugation with anti-CD86 Mab and by 4-5 log upon conjugation with anti-CD80 Mab (Table 4). On L428 cells the pattern of toxicity was the same, but the increase of RIPs cytotoxicity upon conjugation was 1 log lower than on Raji cells Crable 5). No toxicity was observed with free Mabs. The anti-CD80-saporin and anti-CD86-saporin immunotoxins were the most active on cell lines, with $IC_{50}$'s ranging from $2.5 \times 10^{-13}$ M to $5.8 \times 10^{-12}$ M. The immunotoxins made with bouganin and gelonin showed $IC_{50}$'s in the $1.3 \times 1.9 \times 10^{-10}$ M range, when linked to anti-CD86, and in the $4.6 \times 10^{-12}$-$5.7 \times 10^{-11}$ M range, when conjugated to anti-CDBO. The immunotoxins containing anti-CD80 Mab were more active than the corresponding anti-CD86 Mab containing ones, whilst the mixture of the two type of immunotoxins showed an intermediate toxicity. Similar results were obtained using either bouganin, gelonin or saporin, and in both Raji and L428 cell lines. Toxicity of the free RIPs was clearly the highest for saporin, followed by gelonin. Bouganin was clearly the least toxic at both cell lines.

TABLE 4

Effect of immunotoxins on protein synthesis by Raji cell line.

| | anti-CD80 immunotoxins $IC_{50}$ (pM) | anti-CD86 immunotoxins $IC_{50}$ (pM) | anti-CD80 + anti-CD86 immunotoxins $IC_{50}$ (pM) | Free RIPs $IC_{50}$ (nM) |
|---|---|---|---|---|
| Bouganin | 4.61 ($r^2 = 0.99$) | 192 ($r^2 = 1.00$) | 12.2 ($r^2 = 1.00$) | 839 ($r^2 = 0.99$) |
| Gelonin | 56.5 ($r^2 = 1.00$) | 172 ($r^2 = 0.97$) | 82.1 ($r^2 = 0.97$) | 541 ($r^2 = 0.99$) |
| Saporin | 0.253 ($r^2 = 0.99$) | 2.67 ($r^2 = 0.99$) | 1.10 ($r^2 = 1.00$) | 23.6 ($r^2 = 0.99$) |

TABLE 5

Effect of immunotoxins on protein synthesis by L428 cell line.

| | anti-CD80 immunotoxins $IC_{50}$ (pM) | anti-CD86 immunotoxins $IC_{50}$ (pM) | anti-CD80 + anti-CD86 immunotoxins $IC_{50}$ (pM) | Free RIPs $IC_{50}$ (nM) |
|---|---|---|---|---|
| Bouganin | 27.8 ($r^2 = 0.99$) | 129 ($r^2 = 1.00$) | 29.9 ($r^2 = 1.00$) | 49.8 ($r^2 = 1.00$) |
| Gelonin | 17.8 ($r^2 = 1.00$) | 160 ($r^2 = 0.99$) | 31.8 ($r^2 = 0.98$) | 11.4 ($r^2 = 0.99$) |
| Saporin | 0.495 ($r^2 = 1.00$) | 5.84 ($r^2 = 0.99$) | 2.46 ($r^2 = 1.00$) | 4.37 ($r^2 = 0.98$) |

The immunotoxins were also tested for capacity to inhibit clonogenic efficiency. Normal peripheral blood cells were cultured in semisolid medium as previously described (Tazzari et al, *Brit. J. Haematology* 86;97 (1994)). Briefly, $5 \times 10^3$ cells were plated in duplicate in culture medium consisting of 1 ml of Iscove's modified Dulbecco's medium (IMDM), supplemented with 24% FBS, 0.8% BSA, $10^{-4}$ M 2-mercaptoethanol, 2 U of human recombinant erythropoietin (Dompè Biotec, Milan, IT) and 0.2 mM bovine haemin. To measure the optimum clonogenic efficiency, 10% (v/v) of a selected batch of a phytohemoagglutinin-lymphocyte conditioned medium was added.

Figure 6:
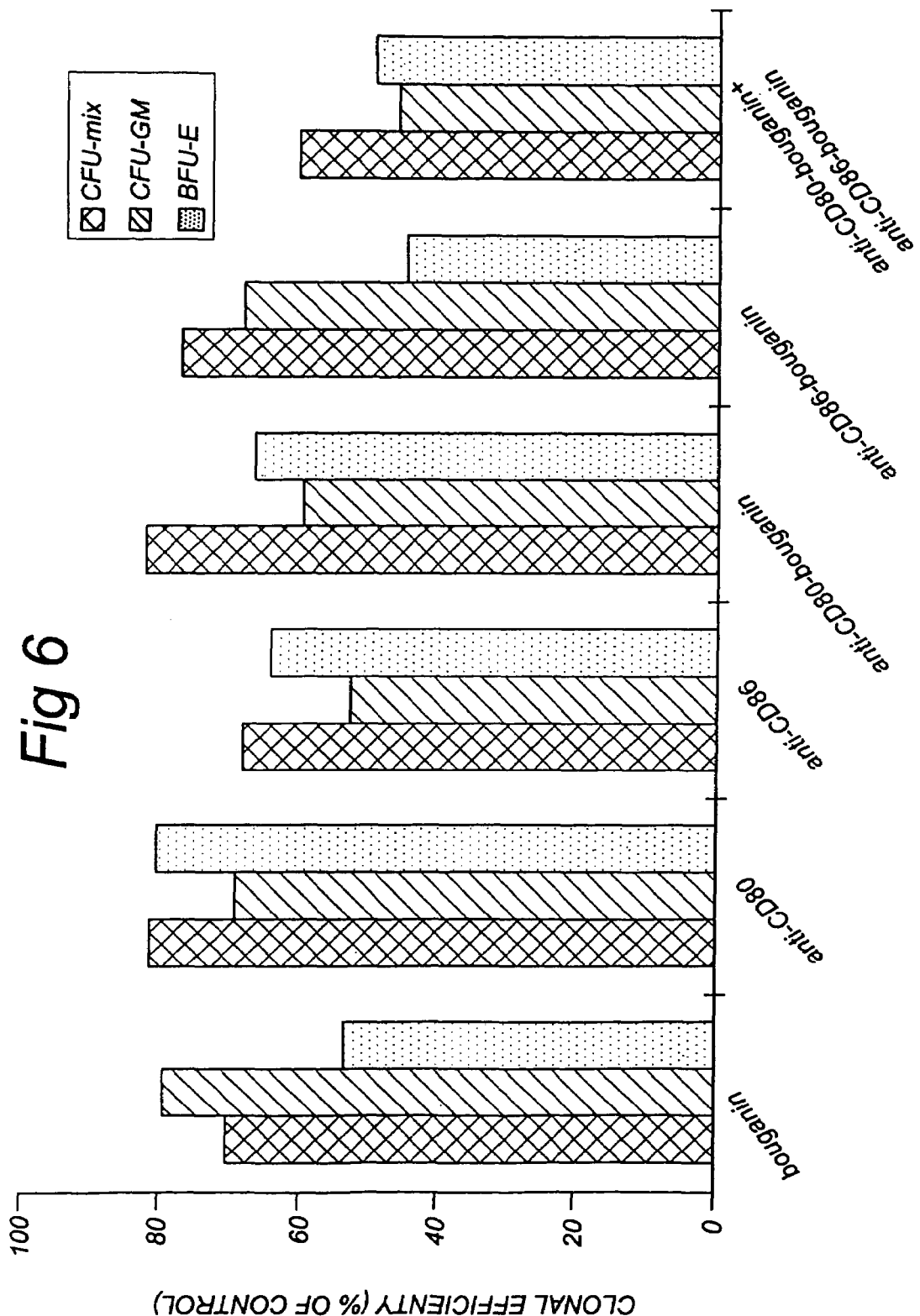
FIG. 6 shows the clonogenicity of CD34$^+$ staminal blood cells after short term exposure to the immunotoxins.

Methylcellulose final concentration was 1.1%. Granulocyte-macrophage colony-forming unit (CFU-GM), erytlroid progenitors (BFU-E) and mixed colonies (CFU-GEMM) were scored after 14 days of incubation at 37° C. in a fully humidified 5% $CO_2$ atmosphere. All cultures were performed in presence of 2 U/ml of erythropoietin. Anti-CD80-bouganin and anti-CD86-bouganin immunotoxins were added to the cultures (continuous exposure) at a final concentration of $10^{-8}$ M as RIP. To control samples the same concentration of Mabs alone or bouganin alone was added. Experiments were also performed by plating highly purified CD34$^+$ cells after 1 h. incubation with $10^{-7}$ M immunotoxins, Mabs or bouganin (short-term exposure). The clonogenic efficiency of CD34$^+$ cells was 7=3%. CD34$^+$ cells were purified from the peripheral blood mono-nuclear fraction, obtained by gradient separation (Lymphoprep, 1077 g/l, Nycomed Pharma, Oslo, Norway). Low density cells were washed twice in phosphate buffer-satine with 1% bovine serum albumin (BSA, Sigma) and CD34$^+$ cells were highly purified by MiniMacs high-gradient magnctic separation column (Milteny Biotec, Bergisch Gladbach, Del.) (Lemoli et al., 1997). To assess the percentage of CD34$^+$ elements, aliquots of CD34$^+$ target cells were retained with the HPCA-2 antibody (IgG a-FITC, Becton Dickinson) directed toward an epitope of CD34 antigen different from the one targeted by the Qbend10 mAb, used with the MiniMacs system. Briefly, CD34$^+$ cells were incubated for 30 min. in the dark at 4° C. with HPCA-2-FITC. Propidium iodide (2 µg/ml) was added for the detection of nonviable cells, which were excluded from analysis. After 2 washes in PBS/BSA, flow-cytometric analysis was performed on a gated population set on scatter properties by using FACScan equipment (Becton Dickinson). A minimum of 10,000 events were collected in list mode on FACScan software. In all experiments the purity of CD34$^+$ cells was >90% and the recovery >80% (Lemoli et al., 1997). A short tern exposure (1 h.) to $10^{-7}$ M concentration of all the tested substances showed an inhibition of CFU-mix, CFU-GM and BFU-e ranging from 20 to 50%. Continuous incubation (14 days) with $10^{-8}$ M concentration of immunotoxins resulted in 52-71% of inhibition, whereas a continuous exposure to the same concentration of free bouganin and Mabs gave 15-49% inhibition (FIG. 6).

The toxicity of short-term exposure to the bouganin-containing anti-CD80 and anti-CD86 immunotoxins was also tested on the clonogenic activity of L428 and Raji cell lines. After 2 washes to remove free conjugates, $2 \times 10^3$ tumour cells were plated in IMDM supplemented with 10% FCS and 1% glutamine and antibiotics. Methylcellulose was added at a final concentration of 1.1%. Aggregates >50 cells were scored with an inverted microscope after 7 days of culture. A complete elimination of L428 clones was reached with immunotoxins or cocktail treatment, whereas on Raji cells the anti-CD80 immunotoxin and the cocktail caused a total reduction of clonogenic growth, but the anti-CD86 did not achieve a complete elimination of clones. Free bouganin, anti-CD80 and anti-CD86 Mabs inhibited clonogenic growth from 0 to 22% (FIG. 7).

Example 8

Molecular Cloning of the Bouganin cDNA

The first step in the molecular cloning of the cDNA for bouganin was the design of degenerate PCR primers. These primers were based on the N-terminal amino acid sequence of bouganin or on the amino acid sequence of an internal peptide fragment of bouganin as are shown in example 3. Combinations of these primers or the individual primers together with an oligo-dT primer were used to amplify DNA fragments encoding bouganin. These fragments were sequenced in order to obtain cDNA sequence information.

Total RNA was isolated by pulverizing leaves of *B. spectabilis* Willd using liquid nitrogen and homogenizing in guanidine thiocyanlate at 10 ml/g leaves. Next, the sample was extracted with phenol/chloroform/isoamyl alcohol, followed by precipitation of the RNA with ethanol. The RNA was washed with 75% ethanol and dissolved in DEPC-treated water. By measurement of the extinction at 260 nm the RNA was quantified. To obtain mRNA the sample was incubated with oligo-dT magnetic beads (Promega, Madison, USA). The mRNA was captured, eluted from the beads and quantified as specified by the manufacturers protocol. First strand cDNA was synthesized by incubation at 37° C. for 1 h. of approximately 1ug mRNA or 10 µg0 in 50 µl mix, consisting of 1×synthesis buffer (50 mM Tris—HCl pH 8.3, 75 mM KCl, 3 mM $MgCl_2$ and 10 mM DTT), 0.5 mM dNTP, random hexamers, M-MLV-reverse transcriptase (USB, Cleveland, Ohio, USA). From this mixture 1-2.5 µl was used as template in PCR reactions using the above described combinations of primers. A standard PCR mixture of 100 µl contained 1×PCR buffer, 2.5 U Taq polymerase, 0.25 mM dNTPs, 250 nM of each primer and cDNA template. The mixture was run in a Perkin-Elmer thermocycler for 30-40 cycles of 1 min. 95° C., 1 min. 55° C.-57° C., and 2 min. 68° C.-72° C. followe by 1 step for 7 min. at 68° C.-72° C. as extension of the PCR product.

Based on the N-terminal amino acid sequence 4 sense and 1 anti-sense degenerate DNA primers were designed. Using appropriate pairs of primers various PCR products were amplified. After analysis on ethidium bromide stained agarose gets it was initially observed that only the combination of primer 102 with 116 yielded a PCR product of expected size.

The sequences of these degenerate primers are set out below using IUB nucleotide codons.

```
Primer 102  5' GGN GAR GCN TAY GAR TAY CCN AC 3'
(SEQ ID NO:
3)
Primer 116  5' GGN GTN CCY TTN GCN AGY TCR TT 3'
(SEQ ID NO:
4)
```

The 65 bp DNA fragment obtained in this way (corresponding to amino acid 10 to 30 of bouganin) was gel-purified and cloned in pCR-Script Cam Sk(+) cloning vector of Stratagene (La Jolla, USA) using the pCR-Script cloning kit according to the manufacturer's protocol. The DNA sequence of the insert was determined and the deduced amino acid sequence based on the resulting DNA sequence matched the experimentally determined N-terminal bouganin amino acid sequence. Below the retrieved sequence is shown.

```
Bouganin                                       (SEQ ID NO: 5)

5' GGG GAG GCC TAC GAG TAT CCC ACT TTT ATA CAA GAT

TTG CGC AAC GAA CTC GCT AAA GGA ACC CC 3'
```

Based on this sequence (SEQ ID NO: 5) the exact oligonucleotide primer 125 (SEQ ID NO: 6) was designed. This primer 125 was used in combination with the degenerate primer 197 (SEQ ID NO: 7), which was based upon the internal bouganin amino acid sequence obtained as described above in example 3. This PCR reaction resulted in a 360 bp fragment. The sequences of the used primers are set out below.

```
Primer 125  5' CTT TTA TAC AAG ATT TGC GCA ACG A 3'
(SEQ ID NO:
6)
Primer 197  5' AAY TCN ARY TTR TAN CAN CC 3'
(SEQ ID NO:
7)
```

The amplified 360 bp product was gel-purified and cloned in pCR-Script Cam Sk(+) cloning vector of Stratagene as described before. Subsequently, the DNA sequence was determined and the amino acid translation was deduced. The clone contains a fragment encoding 120 amino acids of bouganin (residues 17-136). The cDNA sequence and the amino acid sequence deduced from the sequence of this clone are shown in SEQ ID No. 8. Also this deduced amino acid sequence shows limited identity with the amino acid sequences of several other known RIPs.

The partial amino acid sequences depicted in SEQ ID No.'s 1 and 2 (see Example 3) and the deduced partial amino acid sequence depicted in SEQ ID No. 8 were combined to the 149 amino acid sequence shown in SEQ ID No, 9, which represents about 60% of the complete bouganin amino acid sequence.

Example 9

Generation of Single Chain Anti-CD86 Immunotoxin Molecules Containing Bouganin

A single-chain immunotoxin based on anti-CD86 monoclonal antibody and bouganin is obtained using a strategy by which a single chain antibody fragment (scFv) is transferred to an expression cassette system containing the pelB leader signal, the cDNA encoding bouganin and a 6×his purification tag. In this expression plasmid, the scFv is cloned between the pelB leader signal and bouganin. The scFv-bouganin plasmid contains the Lac promoter that allows the expression of the immunotoxins after IPTG (isopropyl 8-D-thiogalactopyranoside) induction. BL21DE3 bacteria are transformed by the $CaCl_2$ method with the expression plasmid and plated on LB plates containing 100 µg/ml ampiciline. One colony is picked and grown overnight in LB containing 100 µg/ml ampiciline. Next day the culture is diluted (1/100) in LB containing 100 µg/ml ampiciline until the $OD_{600}$ reaches 0.5. At this point IFITG (Sigma Chemical Co. St. Louis, Mo., USA)(0.1-1 mM) is added. After 3 h. the cells are harvested for purification of the recombinant scFv-immunotoxin. To purify the proteins from the periplasmic space, first the cells are harvested by centrifugation at 4000×g for 20 min. and resuspended in 30 mM Tris/HCl, 20% sucrose, 0.5 mM EDTA, pH 8.0 and incubated on ice for 10 min. Subsequently the cells are centrifuged at 8000×g for 20 min. and resuspended in ice cold 5 mM $MgSO_4$ followed by incubation on ice for 10 min. After centrifugation at 8000×g the supernatant, which contains proteins from the periplasmic space, is collected and dialysed against 50 mM Na-phosphate, 300 mM NaCl, pH 8.0. This preparation is loaded on a Ni-NTA column (Qiagen, Chatsworth, USA), subsequently the column will be washed with 50 mM Na-phosphate, 300 mM NaCl, 10% glycerol, pH 6.0 and elution of the recombinant immunotoxins is done by 50 mM Na-phospbate, 300 mM NaCl, 10% glycerol, pH 4.0. Column fractions are analysed on SDS-PAGE; fractions containing immunotoxins are pooled and dialysed against suitable buffer.

```
SEQ ID NO:8

1    T TTT ATA CAA GAT TTG CGC AAC GAA TTG GCT AAG GGC ACA CCA GTA    46
    1 (17)     F   I   Q   D   L   R   N   E   L   A   K   G   T   P   V     15

47 TGT CAA CTT CCA GTG ACA CTA CAA ACC ATA GCC GAT GAC AAG CGA TTT    94
       16   C   Q   L   P   V   T   L   Q   T   I   A   D   D   K   R   F    31

95 GTT CTA GTT GAT ATC ACT ACG ACC TCG AAG AAA ACA GTT AAG GTT GCT   142
       32   V   L   V   D   I   T   T   T   S   K   K   T   V   K   V   A    47

143 ATA GAT GTG ACA GAT GTG TAT GTT GTG GGT TAT CAA GAC AAA TGG GAT   190
       48   I   D   V   T   D   V   Y   V   V   G   Y   Q   D   K   W   D    63

191 GGC AAA GAT CGA GCT GTT TTC CTT GAC AAG GTT CCT ACT GTT GCA ACT   238
       64   G   K   D   R   A   V   F   L   D   K   V   P   T   V   A   T    79

239 AGT AAA CTT TTC CCA GGG GTG ACT AAT CGT GTA ACG TTA ACA TTT GAT   286
```

```
                                    -continued
     80  S   K   L   F   P   G   V   T   N   R   V   T   L   T   F   D        95
    287 GGC AGC TAT CAG AAA CTT GTG AAT GCT GCC AAA GTG GAT AGA AAG GAT       334
     96  G   S   Y   Q   K   L   V   N   A   A   K   V   D   R   K   D       111
    335 CTC GAA CTG GGC GTC TAC AAA CTC GAG TT                                363
    112  L   E   L   G   V   Y   K   L   E                                   120 (136)
```

SEQ IN No. 9

Tyr Asn Thr Val Ser Phe Asn Leu Gly Glu Ala Tyr Glu Tyr Pro Thr    16

Phe Ile Gln Asp Leu Arg Asn Glu Leu Ala Lys Gly Thr Pro Val Cys    32

Gln Leu Pro Val Thr Leu Gln Thr Ile Ala Asp Asp Lys Arg Phe Val    48

Leu Val Asp Ile Thr Thr Thr Ser Lys Lys Thr Val Lys Val Ala Ile    64

Asp Val Thr Asp Val Tyr Val Val Gly Tyr Gln Asp Lys Trp Asp Gly    80

Lys Asp Arg Ala Val Phe Leu Asp Lys Val Pro Thr Val Ala Thr Ser    96

Lys Leu Phe Pro Gly Val Thr Asn Arg Val Thr Leu Thr Phe Asp Gly   112

Ser Tyr Gln Lys Leu Val Asn Ala Ala Lys Val Asp Arg Lys Asp Leu   128

Glu Leu Gly Val Tyr Lys Leu Glu Phe Ser Ile Glu Ala Ile Trp Gly   144

Lys Thr Gln Asn Gly                                                149
Note:
Trp-143 is uncertain

---

We claim:

1. An isolated *B. spectabilis* polynucleotide comprising SEQ ID NO: 8, wherein the polynucleotide encodes a polypeptide that has ribosome inactivation protein activity.

2. A recombinant vector comprising the polynucleotide according to claim 1.

3. The recombinant vector of claim 2, further comprising transcriptional and translational control sequences operably linked to the encoding polynucleotide.

4. A host cell transfected with the recombinant vector of claim 2.

5. An isolated *B. spectabilis* polynucleotide encoding a polypeptide comprising SEQ ID NO: 9, wherein the encoded polypeptide has ribosome inactivating protein activity.

6. A recombinant vector comprising the polynucleotide according to claim 5.

7. The recombinant vector of claim 6, further comprising transcriptional and translational control sequences operably linked to the encoding polynucleotide.

8. A host cell transfected with the recombinant vector of claim 6.

* * * * *

UNITED STATES PATENT AND TRADEMARK OFFICE
CERTIFICATE OF CORRECTION

PATENT NO. : 7,479,552 B2
APPLICATION NO. : 10/758902
DATED : January 20, 2009
INVENTOR(S) : Fiorenzo Stirpe et al.

It is certified that error appears in the above-identified patent and that said Letters Patent is hereby corrected as shown below:

Column 1, line 59:
Now reads: "adenosinc"    Should read: -- adenosine --

Column 2, line 1:
Now reads: "derived form"    Should read: -- derived from --

Column 2, line 7:
Now reads: "Olsncs et al."    Should read: -- Olsnes et al. --

Column 2, line 19:
Now reads: "disulfide blind between"    Should read: -- disulfide bond between --

Column 2, line 59:
Now reads: "scientific papers, parents"    Should read: -- scientific papers, patents --

Column 2, line 66:
Now reads: "in vitro or in viva"    Should read: -- in vitro or in vivo --

Column 3, line 7:
Now reads: "The ligand may * molecule"    Should read: -- The ligand may be a protein or a non-protein molecule --

Column 3, line 23:
Now reads: "by the inner in which"    Should read: -- by the manner in which --

Column 3, lines 28, 29:
Now reads: "murinc origin because of the availability of rat or murinc"    Should read: -- murine origin because of the availability of rat or murine --

Column 5, line 3:
Now reads: "dextran, pullulan, dextran"    Should read: -- dextran, pullulan, dextrin --

UNITED STATES PATENT AND TRADEMARK OFFICE
CERTIFICATE OF CORRECTION

PATENT NO. : 7,479,552 B2
APPLICATION NO. : 10/758902
DATED : January 20, 2009
INVENTOR(S) : Fiorenzo Stirpe et al.

It is certified that error appears in the above-identified patent and that said Letters Patent is hereby corrected as shown below:

Column 5, line 15:
Now reads: "forms of carnitinc, arginilie"  Should read: -- forms of carnitine, arginine --

Column 5, line 42:
Now reads: "symbol a is a positive integer"  Should read: -- symbol n is a positive integer --

Column 5, line 62:
Now reads: "Knauf er al"  Should read: -- Knauf et al." --

Column 7, line 36:
Now reads: "in the rabbit reticulocytc"  Should read: -- in the rabbit reticulocyte --

Column 7, line 47:
Now reads "bryodini 1 (SEQ ID No. 16),"  Should read: -- bryodin1 (SEQ ID No. 16), --

Column 7, line 60:
Now reads "anti-CD80 and anti-CD B6"  Should read: -- anti-CD80 and anti-CD86 --

Column7, lines 62, 63:
Now reads: "LA28 cells. Toxic activity ... protein synthesis by the LA28 cells."  Should read: -- L428 cells. Toxic activity ... protein synthesis by the L428 cells. --

Column 7, line 66:
Now reads: "Raji and L248 cell lines"  Should read: -- Raji and L428 cell lines --

Column 8, line 13:
Now reads: "Acia 1216.43 (1993)"  Should read: -- Acia 1216:43 (1993) --

Column 10, line 7:
Now reads: "protein using VB protease"  Should read: -- protein using V8 protease --

UNITED STATES PATENT AND TRADEMARK OFFICE
CERTIFICATE OF CORRECTION

PATENT NO. : 7,479,552 B2
APPLICATION NO. : 10/758902
DATED : January 20, 2009
INVENTOR(S) : Fiorenzo Stirpe et al.

It is certified that error appears in the above-identified patent and that said Letters Patent is hereby corrected as shown below:

Column 10, line 16:
Now reads: "(SEQ ID NO: )"     Should read: -- (SEQ ID NO:2) --

Column 10, line 38:
Now reads: "with phorbot myristate"     Should read: -- with phorbol myristate --

Column 10, line 47:
Now reads: "2 sows that the"     Should read: -- 2 shows that the --

Column 10, line 55:
Now reads: "were from Broebringer"     Should read: -- were from Boehringer --

Column 10, line 58:
Now reads: "sheared and -made"     Should read: -- sheared and made --

Column 10, line 60:
Now reads: "37° DNA was then"     Should read: -- 37°C. DNA was then --

Column 11, line 20:
Now reads: "polynucleotide adenosinc"     Should read: -- polynucleotide:adenosine --

Column 11, line 25:
Now reads: "Agents Chernother"     Should read: -- Agents Chemother --

Column 12, line 12:
Now reads: "Bolognesi er al.,"     Should read: -- Bolognesi et al., --

Column 12, lines 27, 28:
Now reads: "lymphorna and the LA28 cell"     Should read: -- lymphoma and the L428 cell --

Column 12, line 41:
Now reads: "and flow cytomtry."     Should read: -- and flow cytometry --

Column 13, line 33:
Now reads: "by an immodest reaction"     Should read: -- by an imidoester reaction --

Column 13, line 34:
Now reads: "Both Mobs showed"     Should read: -- Both Mabs showed --

UNITED STATES PATENT AND TRADEMARK OFFICE
CERTIFICATE OF CORRECTION

PATENT NO. : 7,479,552 B2
APPLICATION NO. : 10/758902
DATED : January 20, 2009
INVENTOR(S) : Fiorenzo Stirpe et al.

It is certified that error appears in the above-identified patent and that said Letters Patent is hereby corrected as shown below:

Column 13, line 50:
Now reads: "Raji and LA28 cells."   Should read: -- Raji and L428 cells --

Column 14, line 34:
Now reads: "on Raji cells Crable 5.)"   Should read: -- on Raji cells (Table 5). --

Column 14, line 39:
Now reads: "$1.3 \times 1.9 \times 10^{-10}$ M"   Should read: -- $1.3 \times 1.9 \times 10{-10}$ M --

Column 14, line 42:
Now reads: "to anti-CDBO"   Should read: -- to anti-CD80. --

Column 15, line 30:
Now reads: "erytlroid progenitors"   Should read: -- erythroid progenitors --

Column 15, line 42:
Now reads: "was 7=3%"   Should read: -- cells was 7 + 3% --

Column 15, line 46:
Now reads: "buffer-satine with 1%"   Should read: -- buffer-saline with 1% --

Column 15, line 48:
Now reads: "high-gradient magnctic"   Should read: -- high-gradient magnetic --

Column 15, line 52:
Now reads: "epitope of CD34 antigen"   Should read: -- epitope of CD34+ antigen --

Column 15, line 64:
Now reads: "tern exposure (1 h.)"   Should read: -- term exposure (1 h.) --

Column 16, line 37:
Now reads: "thiocyanlate at 10 ml/g"   Should read: -- thiocyanate at 10 ml/g --

Column 16, line 48:
Now reads: "approximately lug mRNA"   Should read: -- approximately 1µg mRNA --

UNITED STATES PATENT AND TRADEMARK OFFICE
CERTIFICATE OF CORRECTION

PATENT NO. : 7,479,552 B2
APPLICATION NO. : 10/758902
DATED : January 20, 2009
INVENTOR(S) : Fiorenzo Stirpe et al.

It is certified that error appears in the above-identified patent and that said Letters Patent is hereby corrected as shown below:

Column 16, line 58:
Now reads: "followe by 1 step"     Should read: -- followed by 1 step --

Column 16, line 66:
Now reads: "gets it was"     Should read: -- gels it was --

Column 18, line 29:
Now reads: "IFITG (Sigma Chemical"     Should read: -- IPTG (Sigma Chemical --

Column 18, line 46:
Now reads: "Na - phospbate"     Should read: -- Na - phosphate --

Signed and Sealed this

Eighteenth Day of August, 2009

David J. Kappos
*Director of the United States Patent and Trademark Office*